US00PP37734P2

(12) United States Plant Patent
Pieters

(10) Patent No.: US PP37,734 P2
(45) Date of Patent: Oct. 6, 2026

(54) ***PHYLLOSTACHYS* PLANT NAMED 'Bokrijk'**

(50) Latin Name: *Phyllostachys kwangsiensis*
Varietal Denomination: Bokrijk

(71) Applicant: Nele Pieters, Genk (BE)

(72) Inventor: Nele Pieters, Genk (BE)

(73) Assignee: LOWLANDS BAMBOO BV, Haarlem (NL)

( * ) Notice: Subject to any disclaimer, the term of this patent is extended or adjusted under 35 U.S.C. 154(b) by 0 days.

(21) Appl. No.: 19/425,995

(22) Filed: Dec. 18, 2025

(51) Int. Cl.
*A01H 5/12* (2018.01)
*A01H 6/46* (2018.01)

(52) U.S. Cl.
USPC ..... Plt./384

(58) Field of Classification Search
USPC ..... Plt./384
See application file for complete search history.

*Primary Examiner* — Susan Mccormick Ewoldt
(74) *Attorney, Agent, or Firm* — Penny J. Aguirre

(57) ABSTRACT

A new cultivar of *Phyllostachys kwangsiensis* plant named 'Bokrijk' that is characterized by its very vigorous and robust growth habit, its strong suckering rooting habit, its pubescence presence on young branches, its lack of flowers and it is not expected to bloom for an estimate of 60 years, its edible shoots, and its good winter hardiness; at least in U.S.D.A. Zones 6a to 10.

2 Drawing Sheets

Botanical classification: *Phyllostachys kwangsiensis.*
Variety denomination: 'Bokrijk'.

BACKGROUND OF THE INVENTION

The present invention relates to a new and distinct cultivar of *Phyllostachys kwangsiensis* and will be referred to hereafter by its cultivar name, 'Bokrijk'. 'Bokrijk' is a new cultivar of bamboo for use as a landscape plant.

'Bokrijk' was discovered by the Inventor as a chance seedling in a nursery production field of *Phyllostachys kwangsiensis* in May of 2018 in Genk, Belgium. The parent plants are therefore unknown.

Asexual propagation of the new cultivar was first accomplished by the Inventor using division in February 2024 in Valkenswaard, Netherlands. Asexual propagation by division has been determined that the characteristics of 'Bokrijk' are stable and reproduced true to type in successive generations.

SUMMARY OF THE INVENTION

The following traits have been repeatedly observed and represent the characteristics of the new cultivar. These attributes in combination distinguish 'Bokrijk' as a unique cultivar of *Phyllostachys.*

1. 'Bokrijk' exhibits a very vigorous and robust growth habit.
2. 'Bokrijk' exhibits a strong suckering rooting habit.
3. 'Bokrijk' exhibits pubescence on young branches.
4. 'Bokrijk' exhibits a lack of flowers and it is not expected to bloom for an estimate of 60 years.
5. 'Bokrijk' exhibits edible shoots.
6. 'Bokrijk' exhibits a good winter hardiness, at least in U.S.D.A. Zones 6a to 10.

The seed parent of 'Bokrijk' is similar to 'Bokrijk' in having a less vigorous less robust growth habit, much less suckers, and less winter hardiness. 'Bokrijk' can be most closely compared to the unpatented plant of the species *Phyllostachys edulis* and *Phyllostachys bambusoides*. Typical plants of *Phyllostachys edulis* are similar to 'Bokrijk' in having high vigor, pubescence on young branches, and edible shoots. Typical plants of *Phyllostachys edulis* differ from 'Bokrijk' in having less winter hardiness and a greater chance of producing flowers as the age of the plants are unknown (plants die after flowering). Typical plants of *Phyllostachys bambusoides* are similar to 'Bokrijk' in having high vigor and pubescence on young branches. Typical plants of *Phyllostachys bambusoides* differ from 'Bokrijk' in having less winter hardiness, young branches that are glabrous, young shoots that are not edible, and a greater chance of producing flowers as the age of the plants are unknown (plants die after flowering).

BRIEF DESCRIPTION OF THE DRAWINGS

The accompanying color photographs illustrates the overall appearance and distinct characteristics of a 2-year plants of the new *Phyllostachys* grown in garden plot in Valkenswaard, The Netherlands.

The photograph in FIG. 1 provides a view of the plant habit of 'Bokrijk'.

Figure 1:
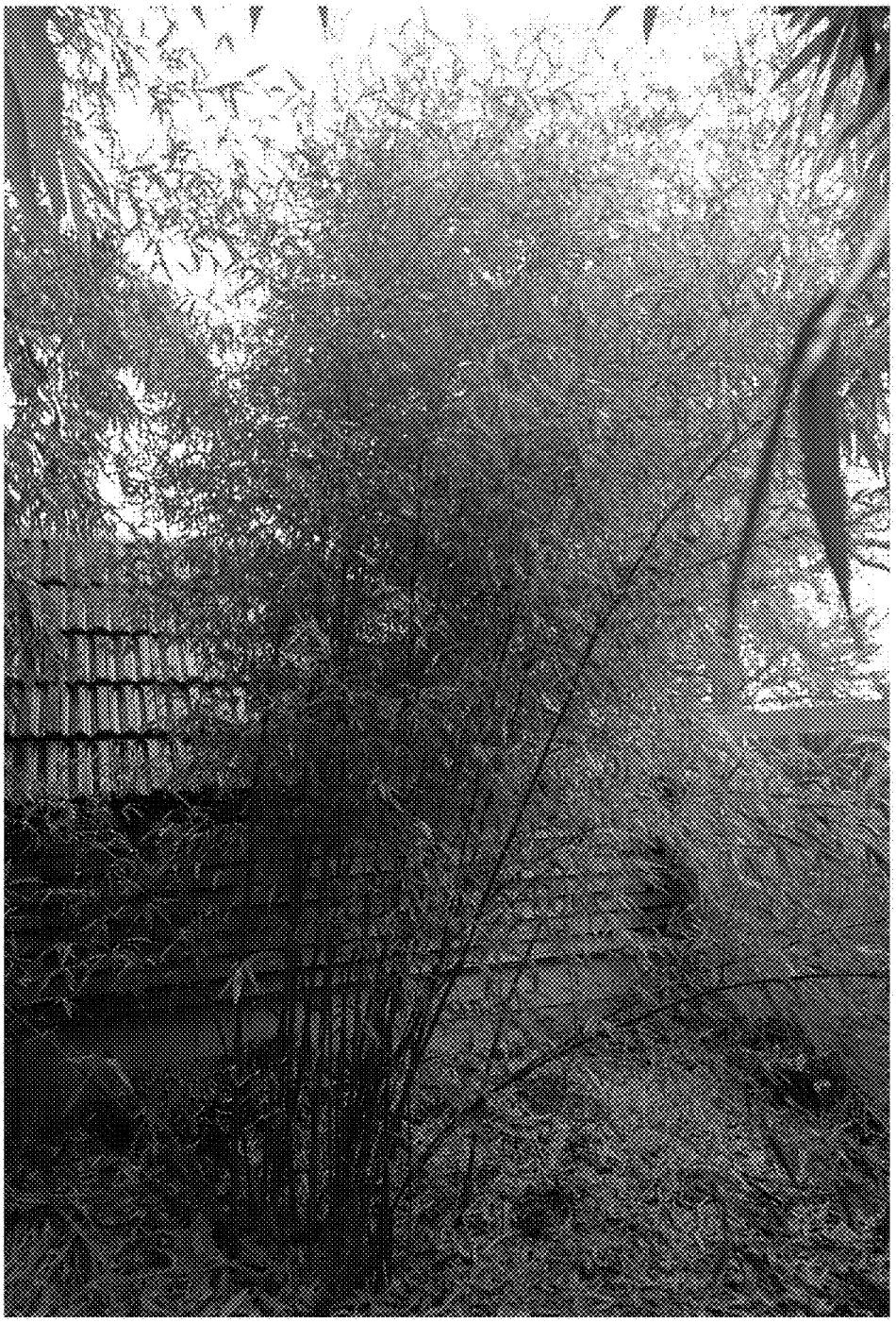
Figure 2:
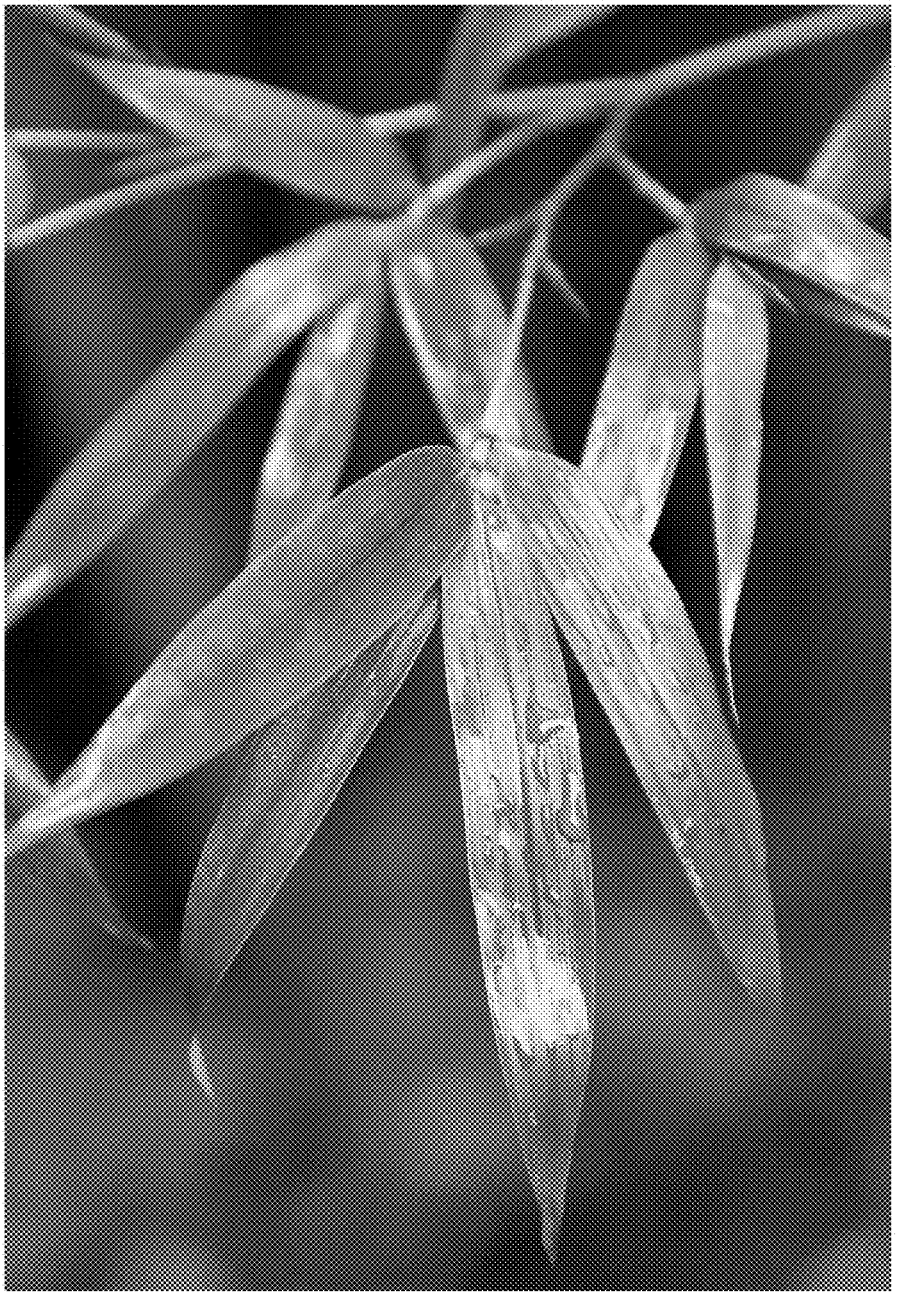

The photograph in FIG. 2 provides a close-up view of the foliage of 'Bokrijk'.

The colors in the photographs are as close as possible with the digital photography techniques utilized and the color values cited in the detailed botanical description accurately describe the colors of the new *Phyllostachys.*

DETAILED BOTANICAL DESCRIPTION

The following is a detailed description of 2-year-old plants of the new cultivar as grown in a garden in Valkenswaard, Netherlands. The phenotype of the new cultivar may vary with variations in environmental, climatic, and cultural conditions, as it has not been tested under all possible environmental conditions. The color determination is in accordance with The 2015 (2019 reprint) Colour Chart of The Royal Horticultural Society, London, England, except where general color terms of ordinary dictionary significance are used.

General description:

*Plant type*.—Perennial bamboo.

*Plant habit*.—Upright, fast growing, strong suckering by rhizomes.

*Plant shape*.—Obovate to broadly obovate.

*Height and spread*.—Reaches an average of 3.9 m in height, 3.45 m in width as a 2-year-old plant as grown in the landscape, as a mature plant in the landscape 10 m in height in height and width.

*Hardiness*.—At least in U.S.D.A. Zones 6a to 10.

*Diseases and pests*.—No resistance or susceptibility to diseases or pests has been observed.

*Root description*.—Rhizomes, 82 cm in length, 2 cm in diameter, smooth and glabrous surfaces, 161A to 162A in color.

*Propagation*.—Division.

Branches description:

*Branch shape*.—Rounded.

*Branches strength*.—Very sturdy.

*Branches color*.—Young; 188B, mature; 146B and 198C, internodes: 137A, lower portion of node covered with a layer of 202D.

*Branches size*.—Main; average of 36.5 m in length and 1.8 cm in diameter, slightly thicker at internodes 2 cm in diameter, lateral; average of 57.7 cm in length and 3 mm in diameter, slightly thicker at internodes 4 cm in diameter.

*Branches surface*.—Smooth and glabrous with a shallow sulcus grove, ligules covered with short soft tomentose hairs; 7 mm in length, a blend of 199B to 199C in color.

*Branches aspect*.—Near vertical, an average of 80° to horizontal.

*Internode length*.—Main; average of 18.6 cm, lateral; average of 7.2 cm.

*Branching*.—Basal main shoots with lateral branches, average of 32 main branches, 24 lateral branches per main branch.

Foliage description:

*Leaf shape*.—Lanceolate.

*Leaf aspect*.—Flat.

*Leaf division*.—Single.

*Leaf arrangement*.—Alternate, growing at the tip of the lateral branches and main shoots.

*Leaf attachment*.—Petiolate.

*Leaf base*.—Attenuate, sheathing.

*Leaf apex*.—Narrow acuminate.

*Leaf fragrance*.—None.

*Leaf venation*.—Parallel, upper surface matches leaf color with base 144C, lower surface matches leaf color with base 137D.

*Leaf margins*.—Entire, un-lobed.

*Leaf surface*.—Both surfaces non-rugose, smooth, glabrous with upper surface very slightly glossy and lower surface matte.

*Leaf size*.—12 cm in length, 1.6 cm in width, sheath; 4.1 cm in length, 2 mm in width.

*Leaf color*.—Young upper surface; 144A, young lower surface; 143B to 143C, mature upper surface 137B, mature lower surface; 137C, sheath; N144A.

*Leaf quantity*.—39 per branch.

*Petioles*.—Average of 3 mm in length and 1 mm in diameter, both surfaces N144A in color and glabrous and smooth with upper surface slightly glossy and lower surface matte.

Inflorescence description: None observed.

It is claimed:

1. A new and distinct cultivar of *Phyllostachys* plant named 'Bokrijk' as herein illustrated and described.

* * * * *